United States Patent [19]

Khoja et al.

[11] Patent Number: 4,820,491
[45] Date of Patent: Apr. 11, 1989

[54] REAGENT TEST STRIP READING INSTRUMENT

[75] Inventors: Mirza A. Khoja, Elkhart; Frank W. Wogoman, South Bend, both of Ind.

[73] Assignee: Miles, Inc., Elkhart, Ind.

[21] Appl. No.: 32,607

[22] Filed: Apr. 1, 1987

Related U.S. Application Data

[62] Division of Ser. No. 649,363, Sep. 11, 1984, Pat. No. 4,689,202.

[51] Int. Cl.$^4$ .............................................. G01N 35/00
[52] U.S. Cl. ..................................... 422/63; 422/104; 422/58; 436/46
[58] Field of Search ................ 198/345, 456, 472, 492, 198/790, 746, 636; 422/63, 65, 66, 67, 58, 104; 436/44, 46–48; 414/18, 749; 211/126; 356/244

[56] References Cited

U.S. PATENT DOCUMENTS

| | | | |
|---|---|---|---|
| 3,578,412 | 5/1971 | Martin | 422/65 |
| 3,918,910 | 11/1975 | Soya et al. | 422/56 |
| 3,999,860 | 12/1976 | Demsky et al. | 356/402 |
| 4,059,405 | 11/1977 | Sodickson et al. | 436/44 |
| 4,402,613 | 9/1983 | Daly et al. | 356/244 X |
| 4,453,807 | 6/1984 | Faulkner et al. | 356/244 X |

*Primary Examiner*—Michael S. Marcus
*Attorney, Agent, or Firm*—Roger N. Coe

[57] ABSTRACT

A multiple reagent test strip-reading instrument having rails extending from a loading area to one or more reading station platforms and then to a waste receptacle, a reciprocating blotter arm which contacts individual reagent strips sequentially placed transversely on the rails in the loading area, moving individual strips along the rails to an indexing strip advancing mechanism which intermittently advances the strips along the rails in spaced parallel relation, and after each advance, allows the strips to dwell for a predetermined time period; individual test strips being thereby sequentially delivered to reading position on the reading station platform where, during the dwell period, they are read by reflectance photometry. After reading, the strips are moved to the waste receptacle. Means is provided for insuring that each test strip is delivered to reading position in registration with the read head of the photometer, and means is also provided for pressing each test strip flat against the reading station platform. The indexing mechanism employs a strip advancing member provided with parallel rows of equally spaced upstanding pegs or fingers, there being guiding and drive means for imparting movement to said member along a vertical orbital path having a generally circular extent and also having a rectilinear extent parallel with the rails, said pegs intersecting the plane of the reagent strips on the rails when said member moves forwardly along said rectilinear extent and being withdrawn from said plane when said member moves rearwardly along said circular extent.

2 Claims, 5 Drawing Sheets

REAGENT TEST STRIP READING INSTRUMENT

This is a division of application Ser. No. 649,363, filed Sept. 11, 1984, now U.S. Pat. No. 4,689,202.

TECHNICAL FIELD

This invention relates to the field of clinical chemistry and more particularly to automated instruments capable of sensing and quantitating the extent of a color change undergone by one or more test areas of a reagent strip following contact thereof with a liquid specimen, such as a urine or blood specimen.

BACKGROUND ART

Reagent srips which comprise one or more test areas capable of undergoing a color change in response to contact with a liquid specimen which may contain one or more constituents of interest have found wide acceptance, particularly in the clinical chemistry field, and have become an extremely useful tool aiding the physician in the diagnosis of disease. In order to afford precise quantitation of such color changes not possible when color comparisons are made with the naked eye, instruments employing reflectance photometry have been developed for reading test strip color changes. Such instruments determine with consistent accuracy the amount of color change, and hence the amount of the sample constituents of interest.

The commercially available strip reading instruments represent a clear advance in the art. However, the speed with which strips can be read therewith is not sufficient adequately to cope with the large numbers of specimens handled by clinical laboratories. This is because in the use of these instruments one strip must be inserted, read and removed from the instrument before the same series of steps can be perford on the next succeeding strip. Moreover, with certain instruments the speed of operation is limited by the requirement for precise placement of the strip in the instrument.

Automation of clinical laboratory procedures has provided significant improvement in the speed with which specimens can be processed. However, the automated instrumentation developed has thus far been limited to laboratory chemical analysis procedures involving the use of liquid reagents, and do not lend themselves to the automated reading of test strips. Representative of such chemical analyzer instruments are those disclosed in U.S. Pat. Nos. 3,578,412 and 4,269,803.

The '412 patent discloses horizontal rails 10 which are vertically reciprocable by a first double-acting air cylinder 28, and horizontal serrated racks 14 which are horizontally reciprocable by a second double-acting air cylinder 34. Plastic multiple cavity liquid sample receptacles 18 are moved by this arrangement past a series of processing stations where various analytical steps are performed. The receptacles have downwardly facing cavity portions at each end, and when the rails 10 are lowered, each such cavity portion fits down over a tooth of a rack 14, necessitating the use of retainer flanges 48 and hold down members 46.

The '803 patent utilizes a ratchet type reciprocable shuttle block 52 having spring loaded fingers 60 for advancing analysis slides 18 along a track 25 past metering and analysis stations. The weight of the slides must be great enough or they must be held down positively by means not shown, to cause the fingers to be tilted downwardly against the bias of the loading springs (not shown) when the shuttle block undergoes retractile movement.

DISCLOSURE OF THE INVENTION

The present invention provides a novel instrument for the expeditious and facile transport, indexing and reading of reagent strips of the type having multiple test areas, some of which areas may have an incubation time which is different from that of other test areas thereof. The instrument has stationary, generally horizontal rails extending from a loading area to and through one or more reading stations and thence to a waste receptacle.

Individual reagent strips to be read by the instrument are sequentially placed transversely on the rails in the loading area, where accuracy of such placement is not a critical factor, there being means including a reciprocating blotter arm for removing excess liquid from each successive strip and for simultaneously orienting the same normal to the rails, as well as endwise, as it is moved along the rails toward the first reading station. As the blotter arm reaches the limit of its advancing movement, an indexing mechanism operating in timed relation with the blotter arm engages the strip contacted by the blotter arm and continues movement of said strip to and through the reading stations.

The indexing mechanism advances the strips in spaced parallel relation a predetermined distance along the rails, and after each incremental advance, allows each strip to dwell for a predetermined time period in its new position. Individual test strips are thereby sequentially delivered to reading position on the first reading station platform where, during the dwell period, certain test areas thereof are read by reflectance photometry. After reading at the first reading station, the strips are advanced progressively to reading position on the second reading station platform where other test areas thereof are read by reflectance photometry.

The indexing mechanism employs a strip advancing member in the form of a removably mounted tray having parallel rows of spaced upstanding pegs or fingers. The rails are formed on a removably mounted stationary base tray which is slotted to permit movement therethrough of the upstanding pegs of the strip advancing member. The trays prevent exposure of the drive and guide mechanism to any specimen which might inadvertently drip from test strips, and when specimen is collected thereby, said trays can be readily removed, washed and replaced.

Strip engaging means is provided at each reading station for pressing each test strip thereat flat against the reading station platform to thereby retain the proper spacing between the strip and the read head. Means is also provided at each reading station for preventing damage to the test strip engaging means thereat which might otherwise occur on removal of the base tray. To this end the strip engaging means is retractably mounted, and interlock means is provided which prevents removal of the base tray unless the strip engaging means is retracted to a position in which it cannot be damaged by such removal.

The indexing mechanism employs guiding and drive means for imparting to the strip advancing member movement along a vertical orbital path having a generally circular extent and also having a rectilinear extent which is parallel with the rails. The pegs of the strip advancing member intersect and project above the plane of reagent strips on the rails when the strip advancing member moves forwardly along the rectilinear extent of its orbital path, and said pegs are withdrawn below the rails during return movement of the strip advancing member along the circular extent of its orbital path. The drive means for the strip advancing member includes means for insuring that termination of movement of the strip advancing member occurs only while the latter is disposed on the circular portion of its orbital path with the pegs thereof retracted below the base tray. This insures that, during shut down, the strip advancing member can be readily removed without interference with the base tray.

BEST MODE FOR CARRYING OUT THE INVENTION

Figure 1:
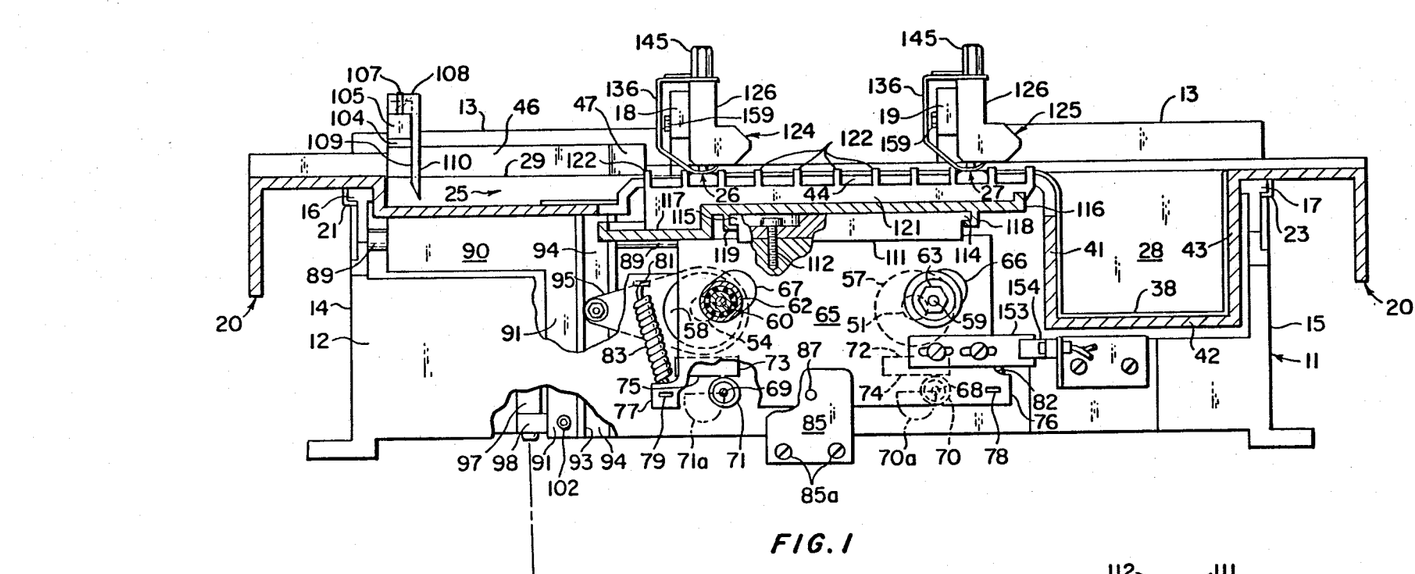
FIG. 1 is a front elevational view of a reagent test strip reading instrument embodying the invention, parts being broken away and shown in section.
Figure 2:
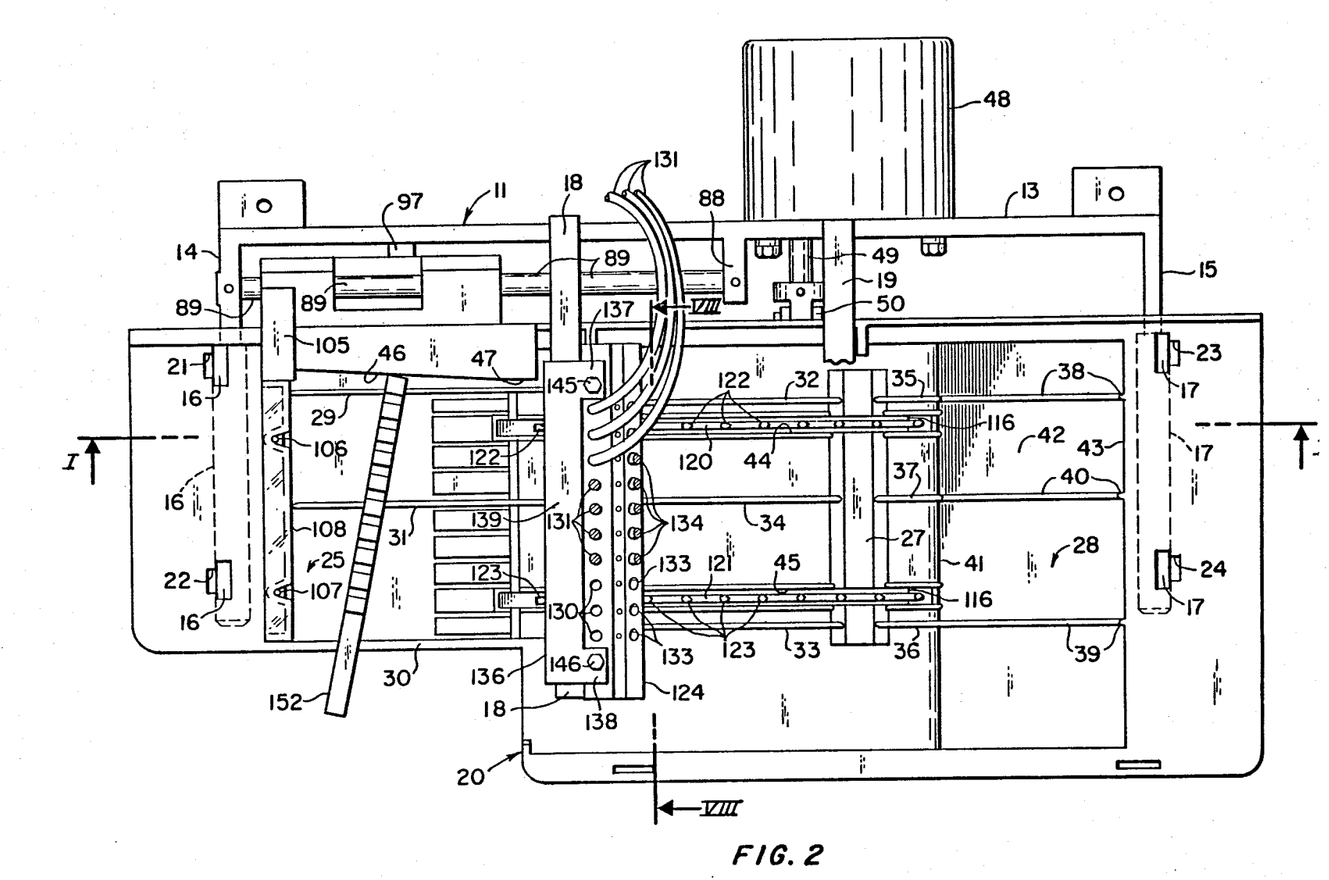
FIG. 2 is a plan view of the instrument shown in FIG. 1, one of the read heads being removed to expose the second reading station platform.
Figure 3:
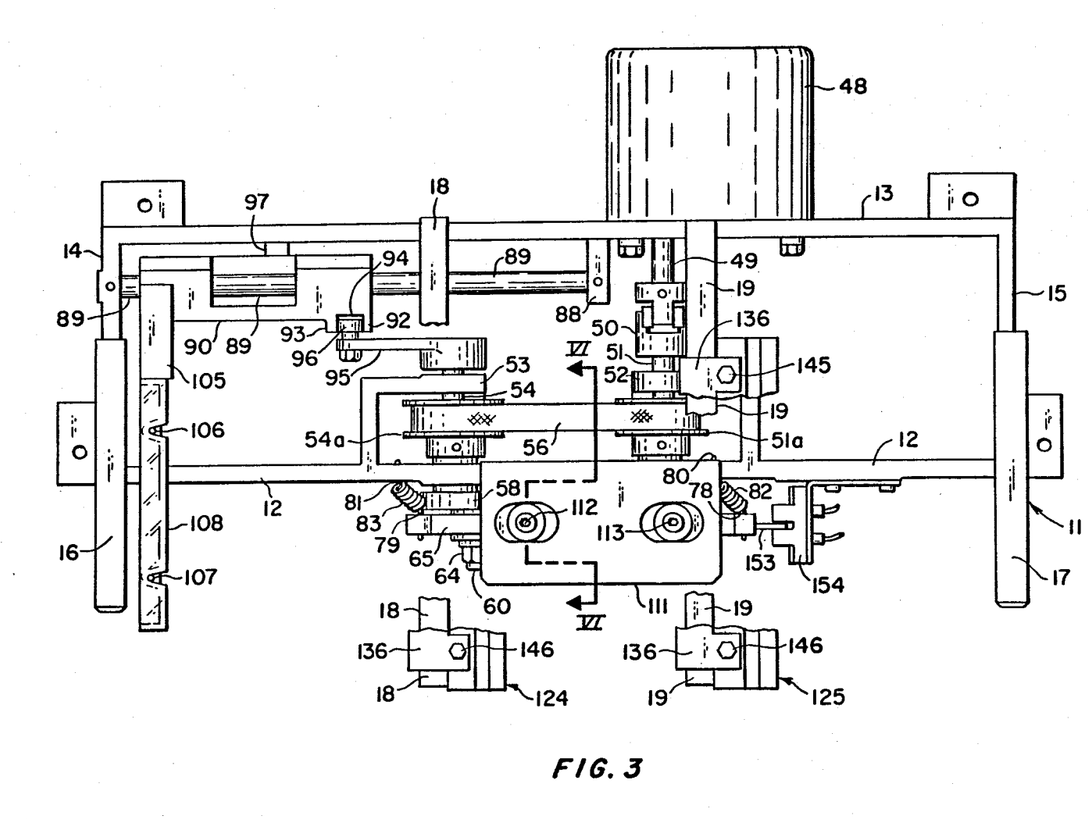
FIG. 3 is a view similar to FIG. 2, with the base tray and the strip advancing member removed to expose the guiding and driving mechanism for the strip advancing member.

Referring now to FIGS. 1 to 3 of the drawings the preferred embodiment of the invention comprises a base frame 11 of generally rectangular configuration which has front and rear wall portions 12 and 13 and end wall portions 14 and 15. The end wall portions 14 and 15 comprise parallel horizontal front to rearwardly extending bar portions 16 and 17 which function as supporting arms for a base tray to be described hereinafter. Projecting forwardly from the rear wall portion 13 is a pair of spaced horizontal bar members 18 and 19 which function as supporting arms for read heads to be described hereinafter.

As best shown in FIGS. 1 and 2, the numeral 20 indicates a fixed base tray which is formed on its underside near one end with guideway portions 21 and 22 which are cooperable with the tray supporting arm 16, and near the other end with guideway portions 23 and 24 which are cooperable with the supporting arm 17. The cooperation of guideways 21 to 24 with arms 16 and 17 is such that the tray 20 can be mounted in operative position by sliding the guideways thereof telescopically over the arms 16 and 17 as the tray 20 is moved transversely inwardly, i.e. rearwardly therealong. Similarly, the tray 20 can be removed from operative position, for example to be emptied and washed, by sliding transverse outward, i.e. forward, movement thereof along the bars 16 and 17. Tray 20 has integral projections (not shown) on its undersurface which are positioned to engage the front end surfaces of the supporting arms 16 and 17, respectively, to thereby define the innermost or operative position of said tray on the frame 11.

The tray 20 has four general areas, i.e. a loading area 25, a first reading station platform 26, a second reading station platform 27, and a waste receptacle 28. The tray 20 is formed in the loading area with spaced parallel generally horizontal rails 29 and 30, the upper surfaces of which are spaced above the adjacent bottom portions of the tray. Rails 29 and 30 are spaced apart a distance approximating the length of the reagent test bearing portion of the reagent test strips to be processed through the instrument. Tray 20 is also formed with an intermediate rail 31 whose upper surface rises from the level of the bottom of the tray at its left hand end to the level of rails 29 and 30 at its right hand end. Rails 29 to 31 extend to the reading station platform 26, at which point the upper surfaces thereof are flush wih said platform.

The reading station platforms 26 and 27 are alike, are parallel and have elongated transversely extending planar rectangular upper surfaces spaced above the level of the adjacent tray bottom portions, The platforms 26 and 27 are of a length and width to provide a flat surface support for the full length and width of at least the reagent test bearing portion of a reagent test strip dispoed thereon.

Tray 20 is formed with spaced horizontal rails 32, 33 and 34 which are generally alined with rails 29, 30, and 31, respectively, and which extend from the platform 26 to the platform 27. The upper surfaces of rails 32 to 34 are spaced above the adjacent tray bottom portions and are generally coplanar with the surfaces of the platforms 26 and 27. Tray 20 is also formed with rails 35, 36 and 37 which extend horizontally from platform 27 to the waste receptacle 28 and are generally aligned with rails 32 to 34 respectively.

The rails thus far described provide generally line contact support for reagent strips extending thereacross and slidably moved therealong in a manner to be hereinafter described. The line contact minimizes adhesion resulting from surface tension of the liquid specimens with which the test areas of the reagent strips are saturated. To similarly minimize contact of test strips in the waste receptacle with the walls and bottom thereof, the tray 20 is formed with rails 38, 39 and 40 which may be extensions of rails 32 to 34, respectively, and which extend vertically along the left hand side wall 41, horizontally along bottom wall 42, and vertically along the right hand end wall 43 of receptacle 28.

The tray 20 is formed with a pair of spaced parallel elongated slots 44 and 45 which extend from the right hand end of the loading area 25 at the left of platform 26 to the right of platform 27 adjacent waste receptacle 28. Slots 44 and 45 extend through the platforms 26 and 27, and to minimize any liquid flow from the tray bottom through said slots, the latter are provided with raised lip portions at the margins thereof.

In the loading area 25 the tray 20 is formed adjacent the rail 29 with a vertical surface portion which extends above the level of the upper surfaces of rails 29 and 30. At its left hand end the surface 46 is spaced from rail 29, and at its right hand end it merges with a vertical surface 47 which is generally parallel with rail 29 and is dipposed closer thereto than the left hand end of surface 46. Surface 46 is positioned for engagement by the inner end portion of reagent test strips placed transversely on rails 29 and 30 in the loading area for a purpose to be described hereinafter.

The instrument is provided with a driving and guiding mechanism which will now be described with reference to FIGS. 1, 3 and 4. A source of driving power in the form of a stepper motor 48 is mounted on the back side of the rear wall 13 of frame 11 and has a drive shaft 49 connected to a flexible coupling 50 which, in turn, is connected to a coaxial shaft 51. Frame 11 is provided with a supporting bearing 52 for shaft 51 spaced from the frame wall 12, as well as with a supporting bearing in wall 12 in which the shaft 51 is rotatably mounted and through which it projects.

Frame 11 is also provided with a supporting bearing 53 spaced from and corresponding to the bearing 52, as well as with a coaxial bearing in the frame wall 12. A shaft 54 is rotatably mounted in and extends through the latter bearing, as well as the bearing 53. The shafts 51 and 54 are parallel and respectively have coaxially fixed thereon between the wall 12 and bearings 52 and 53, like timing pulleys 51a and 54a which are drivingly connected by a timing belt 56, Shafts 51 and 54 are thereby driven at the same speed and in the same direction during operation of the motor 48.

The shafts 51 and 54 have fixed coaxially on the front ends thereof identical wheels 57 and 58 which respectively carry radially offset shafts 59 and 60 on which are mounted actuating members in the form of cylindrical ball bearings 61 and 62 (FIG. 4) respectively, held in place by nuts 63 and 64. The timing of the shafts 51 and 54 is such that the offset shafts 59 and 60 are always at the same angularity during rotation of shafts 51 and 54. For example, when offset shaft 59 is at the apex of its circular travel, shaft 60 is also at the apex of its circular travel.

A vertically disposed generally rectangular plate 65 is formed with shoulder means in the form of a pair of spaced parallel oblong slots 66 and 67 in which the bearings 61 and 62 are slidably positioned, respectively The slots 66 and 67 have substantially the same width as the outer diameter of the bearings 61 and 62, and in the illustrated embodiment, said slots are angled about 45° to the right of vertical. Near its lower edge the plate 65 carries on its inner surface a pair of rearwardly projecting spaced parallel shafts 68 and 69 on which are mounted shoulder means in the form of freely rotatable similar wheels 70 and 71, respectively, shown in FIG. 1.

Projecting forwardly from the front wall 12 of frame 11 are a pair of silar rectaular bosses or shoulder members 72 and 73 having coplanar horizontal lower surfaces 74 and 75, respectively, with which the wheels 70 and 71 coact. The plate 65 is provided with projections 76 and 77 at opposite ends along the lower edge thereof and to which rearwardly projecting eye bolts 78 and 79 are affixed. Corresponding forwardly projecting eye bolts 80 and 81 are affixed to the front wall 12 of frame 11 above the eye bolts 78 and 79, respectively. Opposite ends of a helical tension spring 82 are connected to eye bolts 78 and 80, and opposite ends of a similar spring 83 are connected to eye bolts 79 and 81. The tension of springs 82 and 83 continually exerts an upward force on the plate 65 tending to bias the wheels 70 and 71 into contact with the shoulder surfaces 74 and 75, resptively.

Figure 4:
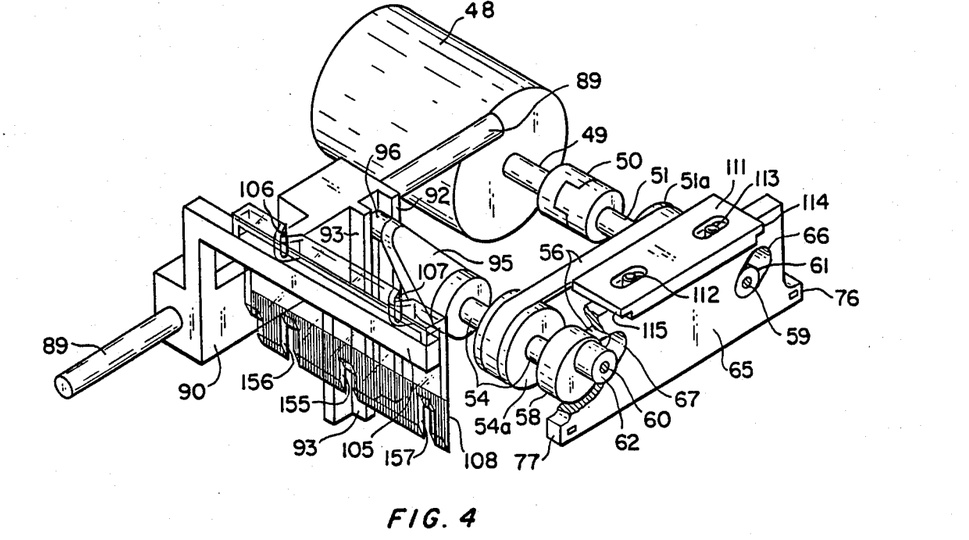
FIG. 4 is a semidiagrammatic perspective view of the drive and guide mechanism for the strip advancing member and the blotter member.

In FIGS. 1 and 4 the bearings 61 and 62 are located at the lower ends of slots 66 and 67, and the plate 65 is in raised position and is generally as far to the right as it can go. This is the reading or dwell position which will be referred to hereinafter. Upon rotation of the shafts 51 and 54 in a clockwise direction, the bearings 61 and 62 travel in a clockwise circular path and impart the same movement to plate 65, moving the wheels 70 and 71 out of contact with the shoulder surfaces 74 and 75 against the bias of springs 82 and 83 during such movement. As the plate 65 and wheels 70 and 71 travel downwardly and thence upwardly toward the left along the aforementioned clockwise circular path, the wheels 70 and 71 are returned to contact with the shoulder surfaces 74 and 75 under the bias of springs 82 and 83, thereby terminating the circular path movement thereof.

Upon contact of wheels 70 and 71 with shoulder surfaces 74 and 75, plate 65 is again in raised position and is generally as far to the left as it can go. During contact of wheels 70 and 71 with surfaces 74 and 75, the plate 65 can not continue to follow the circular path of the bearings 61 and 62. As a result, on continued clockwise rotation of the shafts 51 and 54, the bearings 61 and 62 slide to the upper ends of slots 66 and 67 as they approach their apex position, and only the horizontal component of their circular movement is imparted to the plate 65, moving the latter rectilinearly to the right along a path parallel with surfaces 74 and 75. As bearings 61 and 62 continue their circular travel beyond their apex position, they then slide to the lower end of slots 66 and 67 as the horizontal component of their movement continues the rectilinear movement of plate 65, returning the latter to the position thereof in FIG. 1.

It will be apparent that one revolution of shafts 51 and 54 causes the plate 65 to traverse an orbital path in a vertical plane, which path comprises a rectilinear horizontal extent and a circular extent. The orbital path of plate 65, as traced by the axes of the wheels 70 and 71, is shown in FIG. 1 by the dot and dash lines 70a and 71a.

As part of the control system for the instrument, the plate 65 carries at its right hand edge, as viewed in FIGS. 1 and 3, a switch actuating element 153 for coaction with a switch 154 mounted on the front wall 12 of frame 11. The switch 154 and element 153 can be of any suitable type which will provide actuation of the switch 154, i.e. completion or interruption of a circuit therethrough, by disposition of the plate 65 in the dwell or reading position thereof shown in FIG. 1.

Figure 6:
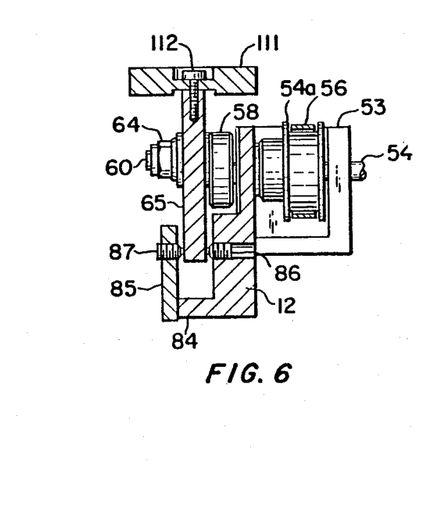
FIG. 6 is a vertical sectional view taken along the line VI—VI of FIG. 3.

Guiding means is provided to maintain the vertical alignment of the plate 65 during its orbital movement. Referring to FIGS. 1 and 6, the front wall of frame 11 has a boss 84 projecting outwardly therefrom below plate 65. Boss 84 extends outwardly beyond plate 65 as shown in FIG. 6, and a vertical plate 85 is fixed at its lower edge, as by screws 85a, to the boss 84. Coaxial set screws 86 and 87 are threaded into suitable bores in wall 12 and plate 85, respectively, and have reduced diameter flat end surface portions which have relatively close fitting sliding engagement with the rear and front surface portions of plate 65 near the lower edge of the latter.

Figure 7:
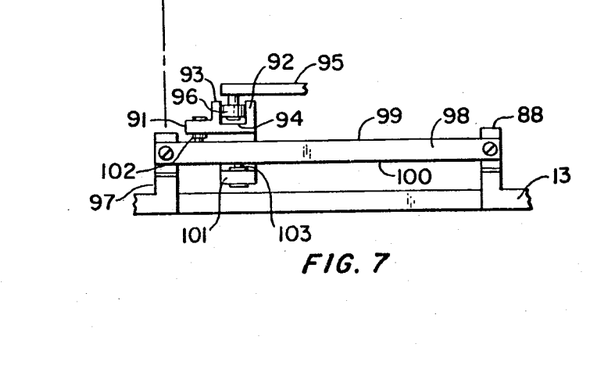
FIG. 7 is a fragmentary bottom plan view illustrating the shuttle block guiding mechanism.

Referring to FIGS. 3 and 7, an elongated vertical rib or boss 88 is formed on the rear wall 13 of frame 11 and is bored at its upper end to receive one end of a horizontal shaft 89, the other end of which is fixed in a suitable bore in end wall 14 of frame 11. A shuttle block 90 is slidably mounted on shaft 89, and depending from the front portion thereof near its right hand end as viewed in FIGS. 1 and 3 is a vertical plate portion 91. Block 90 and its plate portion 91 are formed along the front face thereof with a pair of spaced parallel vertical ribs 92 and 93 which define the margins of an elongated rectangular vertical groove 94.

A crank arm 95 is fixed on the inner end of shaft 54 and carries at its end a cylindrical ball type bearing 96 which has a close fitting slidable fit within groove 94. It will be apparent that, upon one complete rotation of shaft 54, the crank arm will cause one complete reciprocation of the shuttle block 90 along shaft 89 from its position shown in FIGS. 1 and 3 to a position adjacent boss 88 and back to its initial position shown.

Guiding means is provided for preventing any rotational movement of shuttle block 90 during its reciprocating movement. To this end, as best shown in FIG. 7, the rear wall 13 of frame 11 is formed along its lower edge with a forwardly projecting boss 97 to the under side of which is fixed one end of a horizontal bar 98 having parallel planar front and rear vertical surfaces 99 and 100. The opposite end of the bar 98 is fixed to the lower end of the vertical boss 88. The plate portion 91 which depends from the shuttle block 90 is spaced adjacent the front surface 99 of bar 98, and a bar portion 101 depends from shuttle block 90 and has its lower end spaced adjacent the rear surface 100 of bar 98. A set screw 102 is threaded into a suitable bore in the lower end of the plate portion 91 and has a reduced diameter flat end surface in relatively close fitting sliding engagement with the front surface 99 of bar 98. A set screw 103 is threaded into a suitable bore in the lower end of bar portion 101 and has a reduced diameter flat end surface which is in relatively close fitting sliding engagement with the rear surface 100 of bar 98. It is apparent that the coaction of the set screws 102 and 103 with the bar 98 prevents rotational movement of the shuttle block 90 during reciprocation thereof.

Projecting upwardly from the left hand end of the shuttle block 90, as viewed in FIGS. 1 and 3, is a vertical arm 104 which carries at its upper end a forwardly projecting horizontal arm 105 which is parallel with the frame wall 14 and bar 16. Arm 105 carries a pair of spaced upstanding locating and retaining pegs 106 and 107 on its upper surface and provides a support for a blotter member 108. Blotter 108 is generally L-shaped in transverse cross section and has a horizontal extent which overlays the bar 105 and is apertured to receive the locating and retaining pegs 106 and 107. The blotter 108 is formed of solid material, for example organoplastic, and has a depending vertical rectangular plate portion 109 with a generally planar surface 110 formed with a multiplicity of parallel vertical capillary size grooves. Along its lower edge the blotter 108 is notched, as at 155 (FIG. 4) to accomodate the rib 31, and it is also notched as at 156 (FIG. 4) and 157 for a purpose which will appear hereinafter.

Referring to FIGS. 1, 3, 4, and 6, a rectangular horizontal plate 111 is secured, as by screws 112 and 113, to the upper edge of the rectangular vertical plate 65, the plate 111 being recessed to accomodate the heads of said screws below the upper surface of said plate. Adjacent its upper surface, the right and left hand edges of the plate 111 are formed with flanges 114 and 115 which extend from front to rear and provide extensions of said upper surface.

Figure 5:
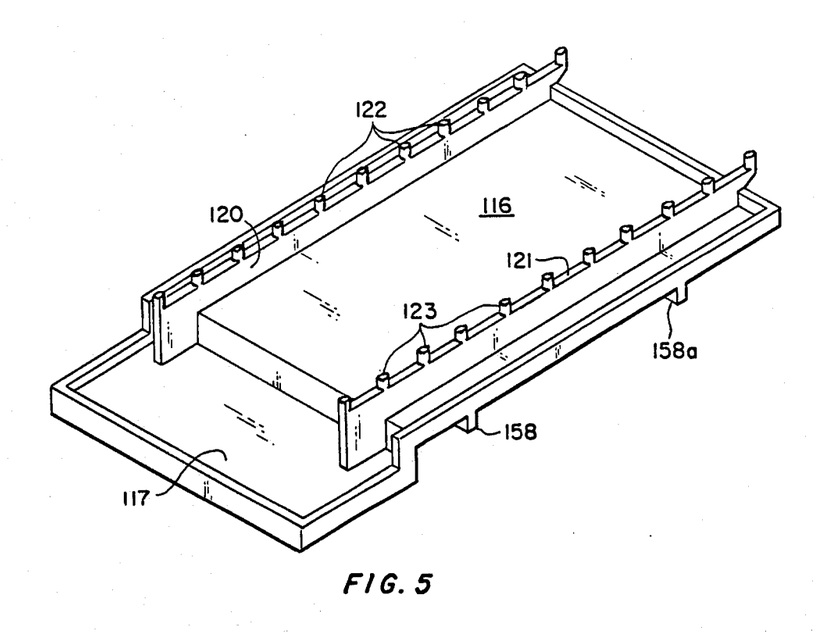
FIG. 5 is a perspective view of the strip advancing member removed from the instrument.

As best shown in FIG. 5, a reagent strip advancing member 116 preferably takes the form of a generally rectangular tray which has a downwardly offset portion 117 at the left hand end thereof and is provided along its edges with a continuous upstanding lip for retention of any liquid which may collect thereon. The strip advancing member 116 is formed on its underside with transversely extending depending parallel brackets 118 and 119 (see FIGS. 1 and 8) which are generally L-shaped in cross section to provide inturned flanges. The brackets 118 and 119 provide guideways for the transverse slidable mounting of member 116 on horizontal plate 111 with the inturned flanges of said brackets engaged beneath the flanges 114 and 115 of plate 111 as shown in FIG. 1. The tray 116 is formed on its underside adjacent its front edge with downwardly projecting stop members 158 and 158a (see FIGS. 5 and 8), which engage the front edge of the horizontal plate 111 to define the operative position of said tray on the plate.

The strip advancing member 116 is formed with a pair of spaced parallel upstanding longitudinally extending ribs 120 and 121 which extend from the offset portion 117 to a bit beyond the right hand end of member 116. The upper edges of the ribs 120 and 121 are horizontal and coplanar, and formed thereon are a plurality of equally spaced upstanding test strip engaging fingers or pegs 122 and 123. In the illustrated embodiment there are eleven pegs 122 and eleven pegs 123. The pegs 122 are transversely aligned with the pegs 123, the pegs in each row being spaced apart a distance sufficient to accommodate a test strip therebetween. The pegs 122 and 123 are advantageously of generally tear drop shape in horizontal cross section to provide on their right hand side, as viewed in FIGS. 2 and 5, only point contact with a reagent strip moved thereby to thereby minimize any adhesion therebetween which might occur due to surface tension of the liquid specimens with which the test areas of the test strips are saturated.

When the strip advancing member 116 is in operative position on the horizontal plate 111, the ribs 120 and 121 thereof are aligned with the slots 44 and 45, respectively, of base tray 20. The slots 44 and 45 are wider than the ribs 120 and 121 and permit travel therethrough of the latter and of the pegs carried thereby without contact with base tray 20.

During operation of the motor 48 the travel of vertical plate 65 along the orbital path illustrated by the dot and dash lines 70a and 71a in FIG. 1 is also imparted to the strip advancing member 116, ribs 120 and 121 and pegs 122 and 123. When the parts are in the position of FIG. 1, member 116 and pegs 122 and 123 are in their uppermost positions wherein said pegs intersect and project above the plane of the upper edges of the rails 29 to 34.

As the motor 48 operates, element 153 (FIGS. 1 and 3) is moved away from switch 154 and the member 116 and its pegs are moved downwardly, toward the left, and then upwardly along the circular extent of the orbital path to cause the pegs 122 and 123 to be withdrawn downardly through the slots 44 and 45 (FIGS. 1 and 2). When member 116 is in its lowermost position along the circular extent of the orbital path, said pegs are spaced below the bottom of base tray 20. As the member 116 reaches the end of the circular extent of the orbital path, it is again in its uppermost position and is as far to the left as it can go. It then moves to the right along the horizontal rectilinear extent of the described orbital path, i.e. parallel with the rails, and is returned to the position thereof shown in FIG. 1, in which the element 153 is again in actuating position with respect to switch 154. In the illustrated embodiment the member 116 and its pegs travel horizontally toward the right 1.2065 cm (0.475 inches) along the rectilinear extent of the orbital path.

In the illustrated embodiment of the invention the time required for the motor to make one complete revolution, and thereby for the member 116 to make one traverse of the orbital path thereof, is 3.8 seconds.

The color changes which the test areas of multiple reagent test strips undergo are sensed, or read, in the instrument by reflectance photometry. To this end a read head 124 (FIGS. 1 and 8 to 10) is suitably vertically adjustably mounted, as by screws 159 and 160, on the right hand vertical face of the support arm 18 in spaced relation above and in alignment with the reading station platform 26. A similar read head 125 (FIG. 1) is similarly vertically adjustably mounted on the right hand vertical face of the support arm 19 in spaced relation above and in alignment with the reading station platform 27. In FIG. 2 the read head 125 is removed to better show the structure therebelow in the area of platform 27.

The read heads 124 and 125 in the illustrated embodiment provide the optics for reflectance photometer reading of a test strip having up to ten equally spaced test areas. Since multiple test strips ordinarily incorporate reagent systems having significantly different incubation times, i.e. the time periods after contact with the liquid specimen during which a color change can develop responsive to the presence of a particular specimen constituent and during which the developed color will remain detectable, the optics of the read head 124 are positioned to read those test areas of a strip which have a predetermined first incubation time. Conversely, the optics of the read head 125 are postioned to read those test areas of a strip which have a predetermined longer incubation time, since a test strip will be read on platform 27 a predetermined time after said strip is read on platform 26.

Figure 8:
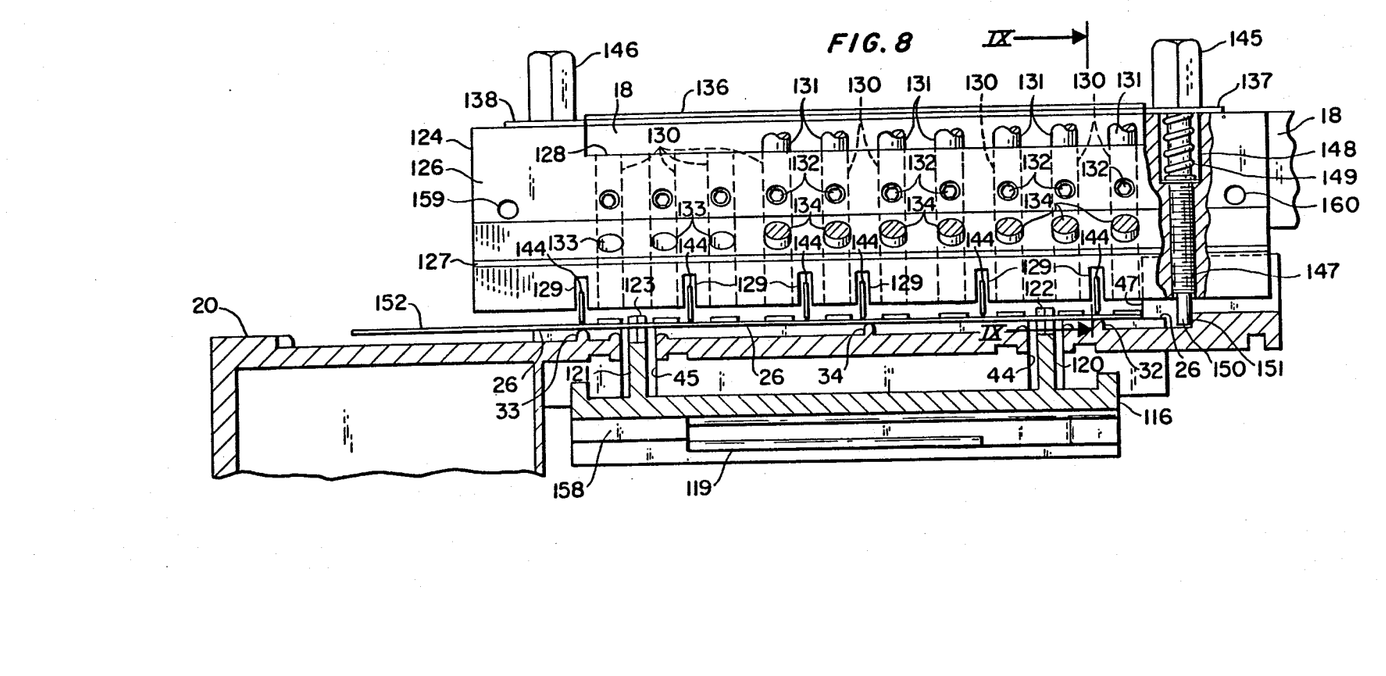
FIG. 8 is an enlarged partial transverse vertical sectional view taken along the line VIII—VIII of FIG. 2, part being broken away and shown in section.
Figure 9:
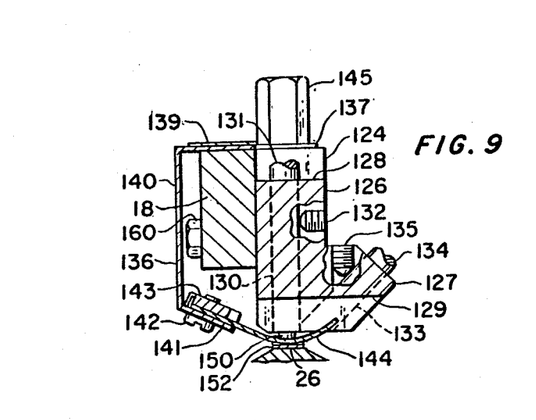
FIG. 9 is a vertical sectional view taken along the line IX—IX of FIG. 8.
Figure 10:
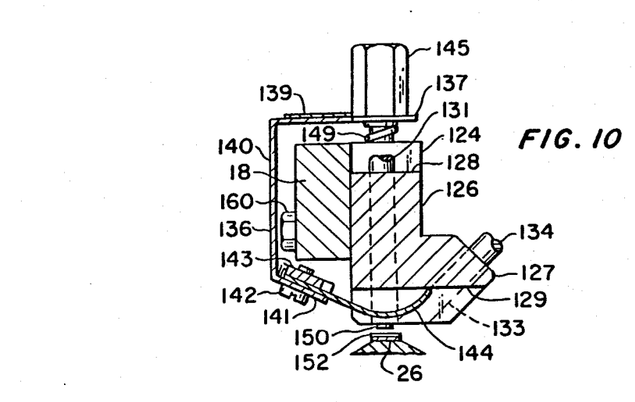
FIG. 10 is a view similar to FIG. 9 showing the strip hold down members in raised position.

Referring to FIGS. 8 to 10 the read head 124 will be described, and it will be understood that the read head 125 is of substantially the same construction. The read head 124 is elongated and is generally L-shaped in cross section as viewed from the front of the instrument, having a main body portion 126 and a horizontally projecting toe portion 127. The upper surface of the body portion 126 is recessed, as at 128, and a plurality of spaced vertical grooves 129, for example six in number, are formed in the bottom of the read head 124 as shown. The main body portion 126 is formed with a plurality of equally spaced vertical through bores 130 which, in the illustrated embodiment, are ten in number. The bores 130 are each adapted to receive one end of a fiber optic element 131 which is held in place by a set screw 132 as shown in FIG. 9. The other end of each element 131 communicates with light sensing means (not shown) in a known matter. Alternatively, the other end of each element 131 can communicate with a source of light (not shown) in a known manner.

The toe portion 127 is formed with a plurality of equally spaced angled through bores 133, each of whose axes is coplanar with that of a corresponding bore 130. The bores 133 are each adapted to receive one end of a fiber optic element 134 which is held in place by a set screw 135 as shown in FIG. 9. The other end of each element 134 communicates with a source of light (not shown) in a known manner. Alternatively the other end of each element 134 can communicate with light sensing means (not shown) in a known manner. It will be observed that there are seven sets of optic elements 131 and 134 in the illustrated embodiment.

Referring also to FIG. 2, a yoke member 136 has a horizontal portion 139 which is U-shaped in plan view and has apertured ear portions 137 and 138 at its opposite ends which normally overlay the upper surface of the read head 124. The remainder of portion 139 normally overlays the upper surface of supporting arm 18, as best shown in FIGS. 2 and 9. Yoke 136 also has a vertical portion 140 which depends from the portion 139 in spaced relation with the supporting arm 18, terminating at its lower edge in an apertured inturned flange 141.

Removably secured to the flange 141, as by screws 142 and one or more cooperable nut members 143, is strip engaging means comprising a plurality of strip engaging or hold down members 144 having arcuate strip-engaging surface portions adapted, when in operative position, to engage the surface of platform 26 or the upper surface of a test strip disposed on said platform. In the illustrated embodiment, the members 144 take the form of wire leaf springs having arcuate. free end portions. As shown in FIG. 8, each of the strip engaging members 144 is aligned with the center line of one of the grooves 129 in the bottom of read head 124.

As also shown in FIG. 8, when the strip engaging members 144 are in their operative positions and engage a test strip disposed on the platform 26, the engaged strip is pressed flat against the platform by said members. This insures that the strip is retained in the proper spacial relationship with the read head 124 while it is disposed on the platform 26.

The yoke 136 is secured to the read head 124 by means of screws 145 and 146 which extend through the apertures in ears 137 and 138, respectively, and are threaded into receiving bores in the read head 124. As shown in vertical section in FIG. 8, the screw 145 is threaded into a vertical through bore 147 which is counterbored at its upper end, as at 148, to accomodate a helical compression spring 149 which coaxially surrounds the screw 145.

A similar counterbore and spring arrangement is associated with the screw 146. However, the lower end of screw 145 is provided with a cylindrical tip portion 150 which projects from the bore 147 and is in position for abutment with a vertical shoulder 151 on base tray 20 when the screw 145 is threaded into the operative position thereof shown in FIGS. 8 and 9. It will be apparent that when screw 145 is in its operative position, the base tray 20 cannot be removed because transverse forward movement thereof is prevented by abutment of shoulder 151 with screw tip 150.

When the screws 145 and 146 are unscrewed, for example to the position of screw 145 in FIG. 10, the compression springs surrounding said screws expand axially to lift the yoke 136 and the members 144 to the positions thereof illustrated in FIG. 10, wherein the strip engaging portions of said members are disposed within the grooves 129 of the associated read head. In this position the members 144 are spaced above the bottom of read head 124, and the tip 150 of screw 145 is spaced above the shoulder 151, to thereby permit removal of the tray 20 by forward movement thereof. The arrangement just described provides an interlock which prevents removal of tray 20 whenever the members 144 are in their operative positions shown in FIGS. 8 and 9, in which positions they would be subject to damage by such removal. The interlock thus permits removal of tray 20 only when the members 144 are lifted to the protected retracted positions thereof shown in FIG. 10.

Operation of the instrument will now be described. It will be assued that the instrument is empty of reagent test strips and that the motor 48 is energized by the control circuit therefor (not shown) to cause clockwise rotation of the shafts 51 and 54, and orbital movement of the strip advancing member 116 as aforedescribed, as well as simultaneous horizontal reciprocating movement of the blotter 108.

It will also be assumed that the reagent test strips to be read have ten test areas thereon and that the reagents of seven of such areas have a relatively short incubation time, whereas the reagents of the remaining three test areas have a relatively longer incubation time. The fiber optics for reading the seven test areas having the shorter incubation time are mounted on read head 124 in positions for alignment with such areas, and the fiber optics for reading the reagent test areas having the relatively longer incubation time are mounted on the read head 125 in positions for alignment with such areas.

During operation of motor 48, blotter 108 and the strip advancing member 116 with its pegs 122 and 123 move generally in opposite directions, i.e. when the pegs 122 and 123 are in their raised positions and are moved to the right (advancing) along the horizontal rectilinear extent of their orbital path, the blotter 108 is simultaneously moved to the left (retracting). As the blotter reaches its most retracted position, the pegs 122 and 123 reach their most advanced position, switch 154 is actuated, and the motor 48 is stopped for a predetermined dwell period, as will be described later herein.

During the aforementioned dwell period the operator places a liquid specimen-saturated reagent test strip, such as the strip 152 (FIG. 2), on the rails 29 and 30 in the loading area 25 of base tray 20 with the inner end of said strip adjacent the angled vertical surface 46. For reasons which will appear, wide variation in the placement of the strip can be tolerated. Assume that the inner end of the strip is in contact with the vertical surface 46 and that the strip is skewed at an angle of other than 90 degrees with respect to the rails 29 and 30. Advancing movement of the blotter 108 caused by subsequent operation of motor 48 at the end of the dwell period will then orient the strip into normality with the rails as the blotter moves into contact with the left hand edge of the strip. As the strip is thus oriented and contact with all of the test areas thereof is made by the blotter 108, any excess specimen in such test areas is removed by the blotter and drips into tray 20.

Simultaneously with the aforementioned orientation of a skewed test strip, contact of the inner end of the strip with the angled vertical surface 46 causes endwise outward movement of the strip as it is advanced along the rails by the blotter 108. The inner end of the strip ultimately moves to and along vertical surface portion 47 which is parallel with the rails, to thereby bring the test areas of the strip into transverse registration with the respective sets of fiber optics in read head 124.

As the blotter 108 reaches its most advanced position, the strip advancing member 116 completes its travel (clockwise as viewed in FIG. 1) along the circular extent of its orbital path by lifting the pegs 122 and 123 to their leftmost raised positions. The leftmost set of pegs 122 and 123 thus arises behind the strip in contact with the blotter 108 when the latter is in its most advanced position. Such disposition of the mentioned pegs prevents the strip from following the blotter during subsequent retractile movement of the latter. As the blotter 108 retracts, interference with movement thereof by the leftmost pegs 122 and 123 is prevented by the notches 156 and 157 (FIG. 4) in the lower edge of the blotter which provide clearance for said pegs.

In the illustrated embodiment of the invention the control system for the motor 48 continues operation thereof which causes simultaneous retractile movement of the blotter 108 and horizontal advancing movement of the pegs 122 and 123 along the recilinear extent their orbital path toward their most advanced position, a distance which, in the illustrated embodiment is 1.2065 cm (0.475 inches). Such rectilinear movement of the pegs 122 and 123 moves the reagent test strip contacted by the leftmost set thereof to the right along the rails the same distance, while at the same time positively maintaining the orientation of the strip in normality with the rails. When the pegs reach the limit of their rectilinear advancing movement, the blotter is about at the limit of its retractile movement, the element 153 actuates the switch 154, and the control system stops motor operation for a dwell period during which the operator can place the next succeeding strip on the rails in the loading area. At the end of the dwell period, the control system resumes operation of the motor, causing the pegs 122 and 123 to travel along the circular extent of their orbital path as the blotter 108 again advances. During such travel, the leftmost set of pegs 122 and 123 is withdrawn downwardly out of contact with the strip to below the tray 20 and is then moved to the left and upwardly to a raised position wherein it is disposed behind the next succeeding strip advanced by the blotter 108 as the latter moved to its most advanced position. Counting from the left, the first mentioned strip is now disposed between the second and third set of pegs 122 and 123, whereas the next succeeding strip is disposed between the first and second set thereof.

In the illustrated embodiment one complete cycle of movement of the pegs 122 and 123 along their orbital path takes 3.8 seconds. Since the strips are at rest on the rails during movement of the pegs along the circular extent of their orbital path, which movement takes about 1.9 seconds, the total dwell time for the strips on the rails is the motor stoppage time of 6.2 seconds plus 1.9 seconds, or about 8.1 seconds. Each time that the blotter 108 moves to its retracted position, which takes place about every 10 seconds, the operator places another test strip on the rails in the loading area 25 of tray 20.

During the next interval of motor operation the first mentioned strip is moved by the aforementioned second set of pegs 122 and 123 under the strip engaging members 144 to reading position on the reading station platform 26 wherein, as shown in FIG. 8, the members 144 engage portions of the strip between the test areas thereof and press the strip flat against the platform 26. The pressing action of the members 144 insures that a constant and predetermined precise vertical spacing exists between the test areas of a strip on the platform 26 and the read head 124. The mounting for the read heads is adjustable, and the position of each read head is normally set when the instrument is assembled.

The first mentioned strip and each succeeding strip rests on the platform 26 for the total dwell time of about 8.1 seconds. During this period of the test areas of the strip are read and the amount of each specimen constituent causing a color change in a test area whose reagents have the relatively short incubation time is sensed by reflectance photometry and is preferably printed out by suitable print out means (not shown).

During each interval of motor operation the first mentioned strip and each succeeding strip is moved along the rails 1.2065 cm (0.475 inches), after which the strips are at rest during the aforementioned total dwell period of about 8.1 seconds. By each interval of movement the strips are disposed between successively advanced pairs of the pegs 122 and 123. The number of the pegs 122 and 123, and the position of the second reading station platform 27 and its associated read head 125 are selected so that the time required for a strip to reach the platform 27 corresponds to the relatively longer incubation time of the test areas of the strips to be read at the platform 27.

One skilled in the art will recognize that to accommodate different incubation times, the mounting for read head 27 can permit adjustment of the position thereof along the rails and tat a strip advancing member 116 with a different number of pegs 122 and 123, as well as a base tray 20 having an appropriately positioned platform 27, can be substituted for those illustrated.

When the first mentioned strip reaches reading position on platform 27, which position corresponds to the reading position thereof on platform 26 illustrated in FIG. 8, the test areas of said strip having the longer incubation time are read during the dwell period. The amount of each specimen constituent causing a color change in each such test area is sensed by reflectance photometry and is also preferably printed out by the aforementioned print out means.

After a test strip is read at the platform 27, further motor operation causes the pegs 122 and 123 to advance the strip along the rails to the waste receptacle 28. In the illustrated embodiment the receptacle 28 can accommodate about 200 strips. Removal of the strips from receptacle 28 is facilitated by the presence of the rails 38 to 40 therein which minimize the possibility of such strips adhering to the receptacle walls.

When the last test strip of a given run has been read on platform 26 and continued motor operation advances said strip off platform 26 toward platform 27, the optics of read head 124 detect the absence of a strip on platform 26 during the next dwell period. The position of the motor when stopped for the dwell period will be termed the zero position thereof. The microprocessor in the control system for the motor 48 is programmed so that when the absence of a strip on platform 26 during a dwell period is detected, operation of the instrument is continued until all of the strips have been read at the platform 27, and deposited in the receptacle, after which the control system rotates the motor about 120° beyond its usual stopping or zero position.

In the illustrated embodiment, the microprocessor of the control system is programmed so that if the read head 124 sees no strip on the platform 26 during any dwell period for a period of 80 seconds, the motor 48 is thereupon rotated 120° beyond its zero position and stopped. This insures that operation of the instrument is continued for the period necessary for reading of the last strip of the run at the platform 27, followed by deposit of said strip in receptacle 28.

When the motor 48 is in the position 120° beyond its zero position, the strip advancing member 116 is in lowered position along the circular extent of its orbital path. In this lowered position, the pegs 122 and 123 are spaced below the adjacent bottom portion of base tray 20, thereby permitting relative transverse movement of the member 116 and tray 20 without interfering contact of any parts thereof. Thus, the control system program always stops the motor 48 at the end of a run in a standby position which permits ready removal of the base tray 20 and member 116 for emptying and/or washing. It will be recalled, however, that the tray 20 cannot be removed until the yoke screws 145 and 146 on read head 124 and the corresponding screws on read head 125 are unscrewed sufficiently to raise the strip engaging members 144 up into the grooves 129 and at the same time to retract the screw tip 150 at each read head above the related tray shoulder 151. As mentioned earlier herein, the interlock thus afforded prevents damage to the strip engaging members 144 which might otherwise occur during removal of tray 20.

The illustrated embodiment of the invention is programmed to read and print out the test results for 360 test strips per hour placed sequentially on the rails in the loading area at 10 second intervals. This is a substantial improvement over the rate at which test strips can be read with prior instrumentation. The instrument permits wide variability in placement of the strips on the rails and automatically orients the strips in precise reading position on the reading station platforms with the test areas of the strips in registration with the respective read head optics.

During such orientation the strips are blotted, and any skewing out of normality with respect to the rails is corrected, and at the same time any endwise movement thereof necessary to align the test areas with the respective read head optics is effected during movement thereof by blotter 108. Finally, when the strip reaches reading position overlaying a reading station platform, it is pressed flat thereagainst by the strip engaging members 144 for the dwell period, during which the raised disposition of the pegs 122 and 123 prevents any skewing of the strip out of alignment with the read head optics while the strip is being read.

The improved instrument is well adapted for reading of test strips whose test areas incorporate reagents having different incubation times. The fiber optic elements can be transferred from one read head to another as necessary to provide reading of each test area at the proper time interval following placeent of the strip on the rails in the loading area 25.

Various changes and modifications may be made in the illustrated embodiment without departing from the spirit of the invention, and all of such changes are contemplated as may come within the scope of the appended claims.

We claim:

1. In combination, a base frame; a tray removably mounted on said base frame, said tray having a reading platform providing a flat surface support for a test strip overlaying said platform; strip engaging means positioned on mounting means adjacent said reading platform, said strip engaging means having an operative position in which a test strip on said platform is engaged thereby at spaced points and is pressed thereby against the platform, said mounting means being above said base frame and tray and being adjustable to effect movement of the strip engaging means between said operative position and a retracted position in which the strip engaging means is spaced from the reading platform; and cooperable shoulder means on said mounting means and on said tray positioned for engagement when said strip engaging means is in its operative position to thereby prevent removal of said tray from the base frame, said shoulder means being disengageable by adjustment of the mounting means effecting movement of the strip engaging means to its retracted position, whereby said tray can be removed from the base frame only when said strip engaging means is in its retracted position.

2. The combination of claim 1, wherein the mounting means for said strip engaging means comprises an adjustable mounting screw having first and second positions corresponding to the operative and retracted positions of the strip engaging means.

* * * * *